(12) United States Patent
Jeon et al.

(10) Patent No.: US 10,474,243 B2
(45) Date of Patent: Nov. 12, 2019

(54) VEHICLE SYSTEM FOR RECOGNIZING A DRIVER'S INTENTION, AND CONTROL METHOD OF THE SAME

(71) Applicants: HYUNDAI MOTOR COMPANY, Seoul (KR); KIA MOTORS CORPORATION, Seoul (KR); LG ELECTRONICS INC., Seoul (KR)

(72) Inventors: Seul Ki Jeon, Suwon-si (KR); Nam Woong Hur, Hwaseong-si (KR); Eung Hwan Kim, Seoul (KR); Jun Bum Park, Suwon-si (KR); Sung Je An, Seongnam-si (KR); Jeong Eun Shin, Seongnam-si (KR)

(73) Assignees: HYUNDAI MOTOR COMPANY, Seoul (KR); KIA MOTORS CORPORATION, Seoul (KR); LG ELECTRONICS INC., Seoul (KR)

( * ) Notice: Subject to any disclaimer, the term of this patent is extended or adjusted under 35 U.S.C. 154(b) by 108 days.

(21) Appl. No.: 15/822,934

(22) Filed: Nov. 27, 2017

(65) Prior Publication Data

US 2019/0011990 A1    Jan. 10, 2019

(30) Foreign Application Priority Data

Jul. 4, 2017  (KR) ........................ 10-2017-0084916

(51) Int. Cl.
*G06F 1/3231* (2019.01)
*G06F 3/01* (2006.01)
(Continued)

(52) U.S. Cl.
CPC .............. *G06F 3/017* (2013.01); *G06F 1/329* (2013.01); *G06F 1/3231* (2013.01); *G06F 3/014* (2013.01);
(Continued)

(58) Field of Classification Search
None
See application file for complete search history.

(56) References Cited

U.S. PATENT DOCUMENTS

| 9,437,064 | B1 * | 9/2016 | Ghabra | .............. G07C 9/00309 |
| 2009/0284345 | A1 * | 11/2009 | Ghabra | .................. B60R 25/24 340/5.61 |

(Continued)

FOREIGN PATENT DOCUMENTS

| KR | 10-2016-0042025 A | 4/2016 |
| KR | 10-2016-0069936 A | 6/2016 |
| KR | 2016-0103707 A | 9/2016 |

*Primary Examiner* — John F Mortell
(74) *Attorney, Agent, or Firm* — Morgan, Lewis & Bockius LLP (57) ABSTRACT

A vehicle system that transmits information about a health state of a driver to a vehicle electronic device communicating with a wearable device includes: a smart key receiving a searching signal from the vehicle electronic device; an acceleration sensor obtaining gesture information about a specific gesture that the driver makes while approaching the vehicle electronic device; a learning processor learning the specific gesture from the gesture information; a controller determining intention of the driver depending on whether the searching signal is received; and depending on whether the obtained gesture information is recognized as the specific gesture and to control on/off of a sensor measuring the information about the health state of the driver; and communication device transmitting the information about the health state of the driver to the vehicle electronic device.

20 Claims, 7 Drawing Sheets (51) Int. Cl.
    *G06F 1/329*       (2019.01)
    *G06F 1/3234*     (2019.01)
    *B60H 1/00*        (2006.01)

(52) U.S. Cl.
    CPC ........ *B60H 1/00657* (2013.01); *G06F 1/3234* (2013.01)

(56) References Cited

U.S. PATENT DOCUMENTS

| | | |
|---|---|---|
| 2015/0046886 A1 | 2/2015 | Goel et al. |
| 2015/0346833 A1* | 12/2015 | Jiang ................ G06F 3/017 345/158 |
| 2015/0362997 A1 | 12/2015 | Hatton |
| 2016/0162007 A1 | 6/2016 | Kim et al. |
| 2017/0196469 A1* | 7/2017 | Han .................... A61B 5/0082 |
| 2017/0282856 A1* | 10/2017 | Riedel .................... B60R 25/25 |

\* cited by examiner

VEHICLE SYSTEM FOR RECOGNIZING A DRIVER'S INTENTION, AND CONTROL METHOD OF THE SAME

CROSS-REFERENCE TO RELATED APPLICATION

This application is based on and claims the benefit of priority to Korean Patent Application No. 10-2017-0084916, filed on Jul. 4, 2017, in the Korean Intellectual Property Office, the disclosure of which is incorporated herein in its entirety by reference.

TECHNICAL FIELD

The present disclosure relates to a vehicle system and a control method, and more particularly, to a vehicle system that saves a battery of a wearable device by predicting whether a driver intends to board a vehicle or to get off the vehicle, and a control method thereof.

BACKGROUND

In the case where a driver holding a smart key approaches a vehicle, the vehicle receives a LF signal of the smart key to automatically release a handle doorlock. However, in this case, it is difficult to determine whether the driver accidentally approaches the vehicle or intends to board the vehicle.

In addition, in the case where a handle doorlock is released by a specific gesture, misrecognition may occur because the specific gesture occurs even in a normal situation. That is, it may not be determined whether a specific gesture was caused by intentional release of the handle doorlock or by a general situation.

In the meantime, in the case where a user wants to use a sensor of a wearable device as needed, there is inconvenience that the user needs to manually turn on or off the sensor of the wearable device because the sensor of the wearable device is manually controlled by the user.

SUMMARY

The present disclosure has been made to solve the above-mentioned problems occurring in the prior art while advantages achieved by the prior art are maintained intact.

The present disclosure may increase a recognition rate of driver's intention to get on and off a vehicle in the case where the driver approaches the vehicle, and may allow a sensor of a wearable device to automatically turn on or off depending on the recognition of the intention to get on and off a vehicle, thereby effectively using a battery.

The technical problems to be solved by the present inventive concept are not limited to the aforementioned problems, and any other technical problems not mentioned herein will be clearly understood from the following description by those skilled in the art to which the present disclosure pertains.

According to an embodiment of the present disclosure, a vehicle system that transmits information about a health state of a driver to a vehicle electronic device communicating with a wearable device includes a smart key receiving a searching signal from the vehicle electronic device, an acceleration sensor obtaining gesture information about a specific gesture that the driver makes while approaching the vehicle electronic device, a learning processor learning the specific gesture from the gesture information, a first controller determining intention of the driver depending on whether the searching signal is received, and depending on whether the obtained gesture information is recognized as the specific gesture and to control on/off of a sensor measuring the information about the health state of the driver, and a communication device transmitting the information about the health state of the driver to the vehicle electronic device.

According to an embodiment, the smart key may be embedded in the wearable device and may be connected in hardware by a connector.

According to an embodiment, the acceleration sensor may obtain the gesture information about an X-axis, a Y-axis, and a Z-axis by sensing a specific gesture of gestures that the driver makes while approaching the vehicle electronic device.

According to an embodiment, the specific gesture may include at least one of an operation of holding a handle of vehicle door by extending a hand wearing the wearable device, an operation of pressing a handle button of the vehicle door, and an operation of pulling the vehicle door toward a body of the driver to open the vehicle door.

According to an embodiment, the vehicle system may further include an analysis processor removing a noise by applying a pre-processing algorithm to the gesture information.

According to an embodiment, if the smart key receives the searching signal from the vehicle electronic device and if a gesture that the driver makes while approaching the vehicle electronic device is recognized as a specific gesture that the learning processor learns, the first controller may determine that the driver intends to board a vehicle and turns on the sensor.

According to an embodiment, if the smart key does not receive the searching signal from the vehicle electronic device, the first controller may determine at least one of that the driver intends to get off a vehicle and that the driver does not intend to board the vehicle and turns off the sensor.

According to an embodiment, the information about the health state of the driver may include at least one of a heart rate, a stress index, and vitality of the driver.

According to an embodiment, the sensor may include a photo-plethysmo graphy (PPG) sensor.

According to an embodiment, the communication device may transmit the information about the health state of the driver to the vehicle electronic device by using Bluetooth Low Energy (BLE).

According to an embodiment, if turning off the sensor, the first controller may turn off the communication device.

According to an embodiment, if the communication device transmits the information about the health state of the driver to the vehicle electronic device, a second controller of the vehicle electronic device may allow a display of the vehicle electronic device to output the information about the health state of the driver.

According to an embodiment of the present disclosure, a control method of a vehicle system that transmits information about a health state of a driver to a vehicle electronic device communicating with a wearable device includes receiving, by a smart key embedded in the wearable device, a searching signal from the vehicle electronic device, determining whether a specific gesture that a driver makes while approaching the vehicle electronic device is a learned specific gesture, if the specific gesture that the driver makes while approaching the vehicle electronic device is the learned specific gesture, determining that the driver intends to board a vehicle, if it is determined that the driver intends to board the vehicle, operating a sensor measuring information about the health state of the driver, and transmitting the information about the health state of the driver to the vehicle electronic device.

According to an embodiment, the receiving of the searching signal from the vehicle electronic device may include, if the searching signal is not received, determining at least one of that the driver intends to get off a vehicle or that the driver does not intend to board the vehicle and allowing the sensor not to operate.

According to an embodiment, the determining of whether the specific gesture that the driver makes while approaching the vehicle electronic device is the learned specific gesture may include collecting gesture information about the specific gesture, removing a noise by applying a pre-processing algorithm to the gesture information, processing the gesture information, learning the specific gesture, and recognizing the learned specific gesture.

According to an embodiment, the collecting of the gesture information may include obtaining and collecting, by an acceleration sensor of the wearable device, the gesture information about an X-axis, a Y-axis, and a Z-axis.

According to an embodiment, the specific gesture may include collecting at least one of an operation of holding a handle of a vehicle door by extending a hand wearing the wearable device, an operation of pressing a handle button of the vehicle door, and an operation of pulling the vehicle door toward a body of the driver to open the vehicle door.

According to an embodiment, the recognizing of the learned specific gesture may include recognizing that a specific gesture that the driver makes when approaching the vehicle electronic device is the learned specific gesture.

According to an embodiment, the operating of the sensor measuring the information about the health state of the driver may include measuring, by the sensor, information including at least one of a heart rate, a stress index, and vitality of the driver.

According to an embodiment, the method may further include, after the transmitting of the information about the health state of the driver to the vehicle electronic device, allowing, by a controller of the vehicle electronic device, display of the vehicle electronic device to output the information about the health state of the driver.

BRIEF DESCRIPTION OF THE DRAWINGS

The above and other objects, features and advantages the present disclosure will be more apparent from the following detailed description taken in conjunction with the accompanying drawings.

DETAILED DESCRIPTION

Hereinafter, exemplary embodiments of the present disclosure will be described in detail with reference to the accompanying drawings. In the drawings, the same reference numerals will be used throughout to designate the same or equivalent elements. In addition, a detailed description of well-known features or functions will be ruled out in order not to unnecessarily obscure the gist of the present disclosure.

In describing elements of exemplary embodiments of the present disclosure, the terms 1st, 2nd, first, second, A, B, (a), (b), and the like may be used herein. These terms are only used to distinguish one element from another element, but do not limit the corresponding elements irrespective of the order or priority of the corresponding elements. Unless otherwise defined, all terms used herein, including technical or scientific terms, have the same meanings as those generally understood by those skilled in the art to which the present disclosure pertains. It will be understood that terms used herein should be interpreted as having a meaning that is consistent with their meaning in the context of this disclosure and the relevant art and will not be interpreted in an idealized or overly formal sense unless expressly so defined herein.

Figure 1:
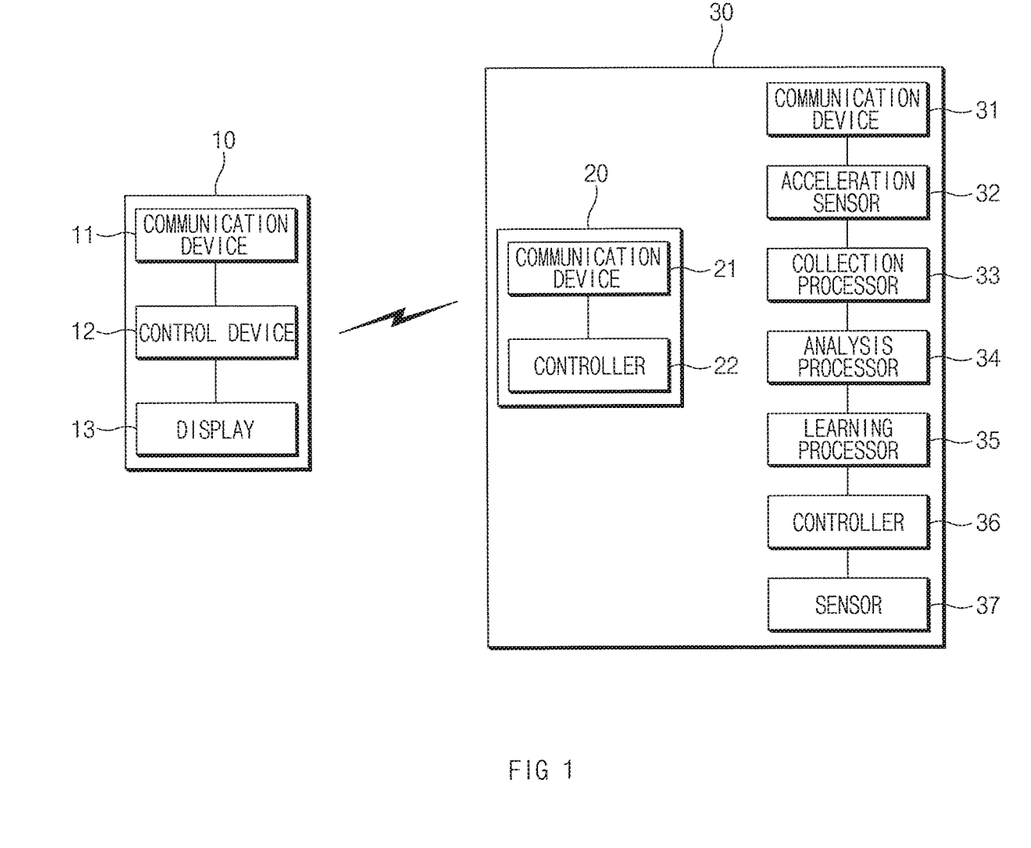
FIG. 1 is a block diagram illustrating a vehicle system, according to an embodiment of the present disclosure.

FIG. 1 is a block diagram illustrating a vehicle system, according to an embodiment of the present disclosure.

As illustrated in FIG. 1, the vehicle system according to an embodiment of the present disclosure may include a vehicle electronic device 10 and a wearable device 30. In addition, the vehicle electronic device 10 may be mounted in a vehicle and may communicate with the wearable device 30. For example, the vehicle electronic device is integrated with a center fascia. The vehicle electronic device 10 may include AVN, navigation, autonomous driving device.

The vehicle electronic device 10 may include a communication device 11, a controller and a display 13.

The communication device 11 of the vehicle electronic device 10 may include a Low Frequency (LF) communication unit and a Radio Frequency (RF) communication unit.

The LF communication unit of a vehicle may transmit a LF signal to various types of electronic devices outside the vehicle over a LF communication network. The LF signal includes a searching signal, which the LF communication unit transmits to a periphery (within a distance where the LF communication is reachable), to determine whether a smart key is within a range in which LF communication is possible from the vehicle.

The RF communication unit of the vehicle receives a RF signal transmitted by various types of electronic devices outside the vehicle over a RF communication network. The RF signal includes a searching response signal transmitted by the smart key to the vehicle such that the vehicle verifies that the smart key receives the searching signal from the vehicle. According to an embodiment of the present disclosure, information about a health state of a driver and the driver's intention to board the vehicle may be received from the wearable device 30 by using Bluetooth Low Energy (BLE).

The controller 12 may include an electronic control unit (ECU) and may control the LF communication unit such that the LF communication unit of the vehicle transmits the searching signal. Furthermore, the RF communication unit may be controlled such that the RF communication unit of the vehicle receives the searching response signal, and may control the RF communication unit such that the RF communication unit receives the information about the health state of the driver from the wearable device 30. The controller 12 may control the lock/unlock of the steering wheel, may control the lock/unlock of a start/stop button for controlling the start/stop of the vehicle, and may control the lock/unlock of a trunk.

The display 13 may output the information about the health state of the driver received from the wearable device 30. The display 13 may include a cluster or audio video navigation (AVN) of the vehicle. That is, the information about the health state of the driver may be output through the cluster or the AVN.

According to an embodiment of the present disclosure, a smart key 20 may be embedded in the wearable device 30 and may be connected in hardware by a connector. That is, a wearable board and a board of the smart key 20 in the wearable device 30 may be connected by the connector. In detail, information indicating that the smart key 20 received the searching signal may be transmitted through one physical pin of the connected connectors.

The smart key 20 may include a communication device 21 and a controller 22.

The communication device 21 of the smart key 20 may include a LF communication unit and a RF communication unit.

The LF communication unit of the smart key 20 receives a LF signal transmitted by various types of electronic devices outside the smart key 20 over the LF communication network. The LF communication unit of the smart key 20 may receive the searching signal that the vehicle transmits.

The RF communication unit of the smart key 20 transmits the RF signal to various types of electronic devices outside the smart key 20 over the RF communication network. The RF communication unit of the smart key 20 may transmit a searching response signal for responding to the searching signal of the vehicle to the vehicle.

The controller 22 may control the LF communication unit such that the LF communication unit of the smart key 20 receives the searching signal. Moreover, the controller 22 may control the RF communication unit such that the RF communication unit of the smart key 20 transmits the searching response signal.

The wearable device 30 may include a communication device 31, an acceleration sensor 32, a collection processor 33, an analysis processor 34, a learning processor 35, a controller 36, and a sensor 37. The communication device 31, the acceleration sensor 32, the collection processor 33, the analysis processor 34, the learning processor 35, the controller 36, and the sensor 37 are electric circuitries which perform various functions described below by execution of instructions embedded therein.

The communication devices 11, 21 and 31 may transmit and receive wireless signals including data to and from a terminal within a distance from the communication devices through communication schemes, such as Low Frequency (LF), a Radio Frequency (RF), Wireless LAN, Wi-Fi, Bluetooth, Zigbee, Wi-Fi Direct (WFD, Ultra wideband (UWB), infrared Data Association (IrDA), Bluetooth Low Energy (BLE), and Near Field Communication (NFC).

The communication device 31 may receive the result of the searching signal that the communication device 21 of the smart key 20 receives and may transmit the result of the searching to the controller 36. Further, the communication device 31 may transmit the information about the health state of the driver, which the wearable device 30 measures through the sensor 37, to the vehicle electronic device 10. The information about the health state of the driver may be transmitted to the vehicle electronic device 10 by using the BLE.

The acceleration sensor 32 may obtain gesture information about an X-axis, a Y-axis, and a Z-axis by sensing a specific gesture, which the driver makes while approaching the vehicle. Here, the specific gestures may include an operation of opening a door of the vehicle. The operation of opening the door of the vehicle may be roughly defined as an operation of three steps.

A. An operation of holding the handle of the vehicle door by extending the hand wearing a wearable device.

B. An operation of pressing a handle button of the vehicle door.

C. An operation of pulling the vehicle door toward a body of the driver to open the vehicle door.

The collection unit 33 collects data of a specific gesture that the acceleration sensor 32 senses.

The analysis processor 34 analyzes gesture information of the sensed gesture of the driver.

Firstly, the analysis processor 34 may apply a pre-processing algorithm to the gesture information, thereby reducing an effect the noise of pieces of gesture information. A low pass filter (LPF), a Gaussian filter, or a moving average filter may be applied to reduce the effect on the noise.

In addition, the analysis processor 34 may apply a Dynamic Time Warping (DTW) algorithm to the pieces of gesture information, in which the effect on the noise is reduced, to process the data. Detailed descriptions will be given with reference to FIGS. 2A and 2B.

Figure 2A:
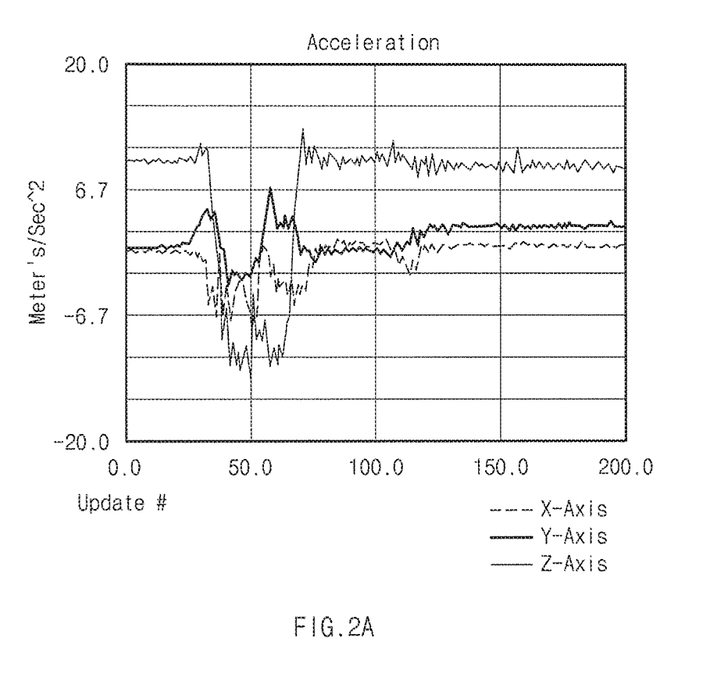
FIGS. 2A and 2B are graphs illustrating gesture information about a driver specific gesture for each timing, according to an embodiment of the present disclosure.
Figure 2B:
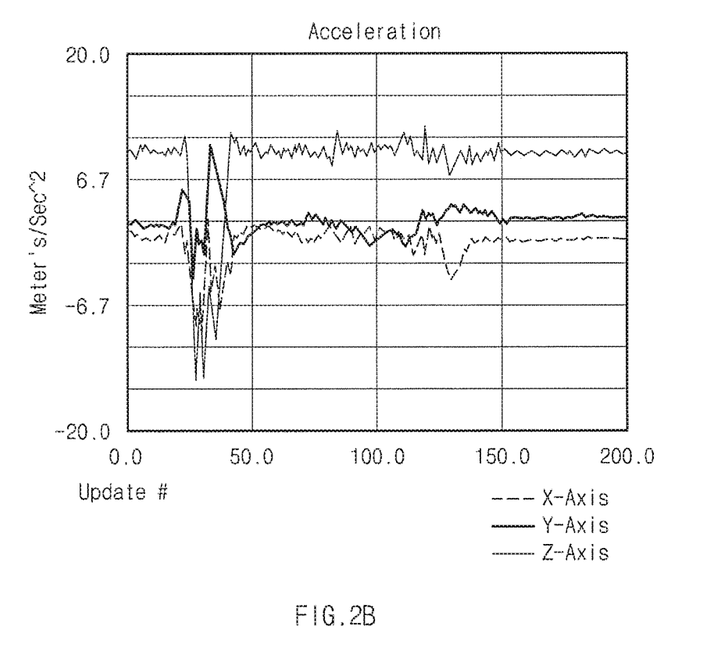

FIGS. 2A and 2B are graphs illustrating gesture signal about a driver specific gesture for each timing, according to an embodiment of the present disclosure. As illustrated in FIGS. 2A and 2B, since an operation of opening a vehicle door is nearly similar for respective drivers, a pattern of data may be similar. However, a time period during which the operation is performed may be different. It is understood that FIG. 2A is a graph illustrating information about a gesture, which is slowly made, and it is understood that FIG. 2B is a graph illustrating information about a gesture, which is quickly made. Similarity is measured by applying a DTW algorithm to pieces of data associated with operations performed during different time periods. The pieces of data having the similarity are processed through reconstruction.

Figure 3:
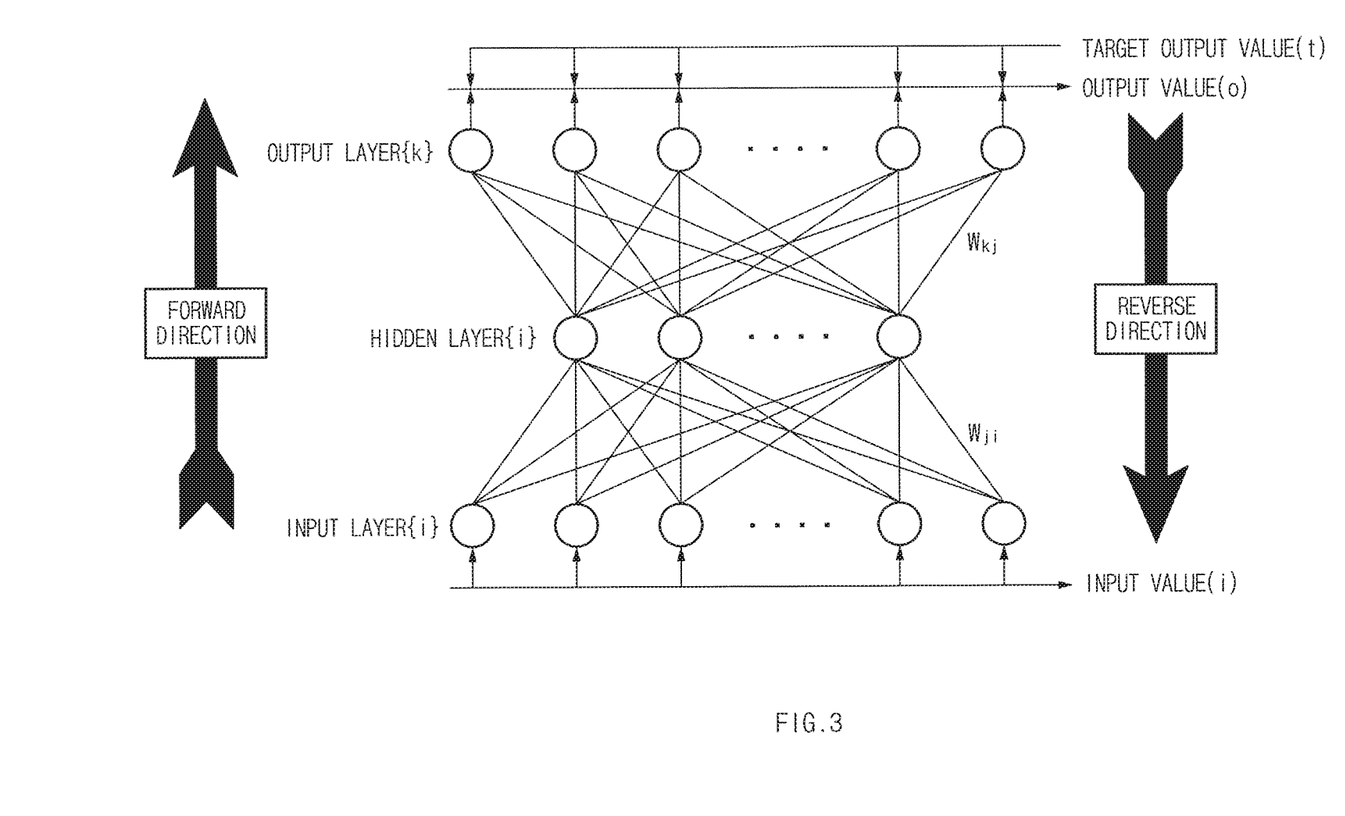
FIG. 3 is a view illustrating neural network algorithm structure for learning a specific gesture of a driver, according to an embodiment of the present disclosure.
Figure 4:
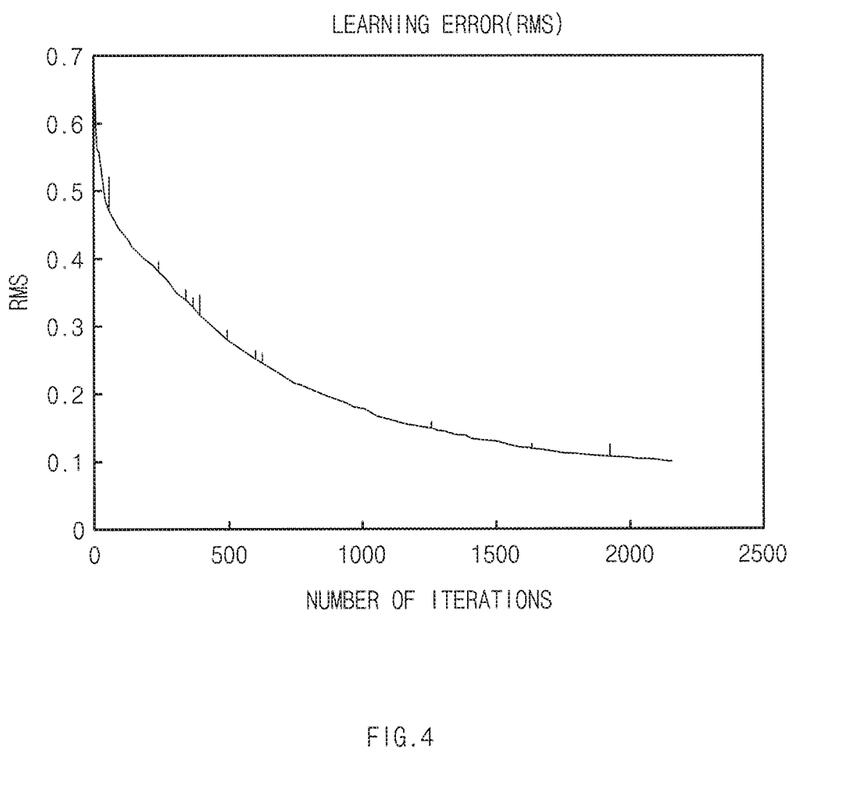
FIG. 4 is a graph illustrating a target value of a specified learning error during learning using a neural network algorithm.

The learning processor 35 may learn data, which is processed through the applying of the DTW algorithm, by using a neural network algorithm or deep learning. The learning processor 35 may learn a specific gesture. FIG. 3 is a view illustrating a neural network algorithm structure for learning a specific gesture of a driver, according to an embodiment of the present disclosure. FIG. 4 is a graph illustrating a target value of a specified learning error during learning using a neural network algorithm. Since the learning about a specific gesture is not made indefinitely, the learning may be made on data (refer to FIG. 4) obtained until a learning error converges on a target value. The learning may be ended in the case where the learning error converges on the target value. The target value may be set by using Root Mean Square (RMS) or Least Mean Square (LMS). That is, according to an embodiment of the present disclosure, when the target value of the learning error is set to 0.1 and the learning error becomes 0.1, the learning may be ended by stopping the iteration for the learning.

In the case where the smart key 20 receives a searching signal (a LF signal), which is received because the smart key 20 approaches a vehicle, from the communication device 31 and the gesture information obtained from the acceleration sensor 32 is recognized as a specific gesture learned by the learning processor 35, the controller 36 may determine that a driver wearing a wearable device intends to board the vehicle and may control all sensible sensors of the wearable device 30 such that all the sensible sensors operate.

In addition, in the case where the smart key 20 does not receive the searching signal (the LF signal) from the communication device 31 because moving away from the vehicle electronic device 10, the controller 36 may determine that the driver wearing the wearable device does not intend to board the vehicle or may determine that the driver wearing the wearable device intends to get off the vehicle. The controller 36 may control all sensible sensors except the acceleration sensor 32 of the wearable device 30 not to operate.

The sensor 37 may include a photo-plethysmo graphy (PPG) sensor. In the case where the controller 36 determines that the driver intends to board the vehicle, the sensor 37 measures a heart rate, a stress index, and vitality of the driver by using the PPG sensor. It may take about one minute for the measurement.

The controller 36 may allow the communication device 31 to transmit information about a health state of the driver, which is measured by the sensor 37, to the vehicle electronic device 10.

Figure 5:
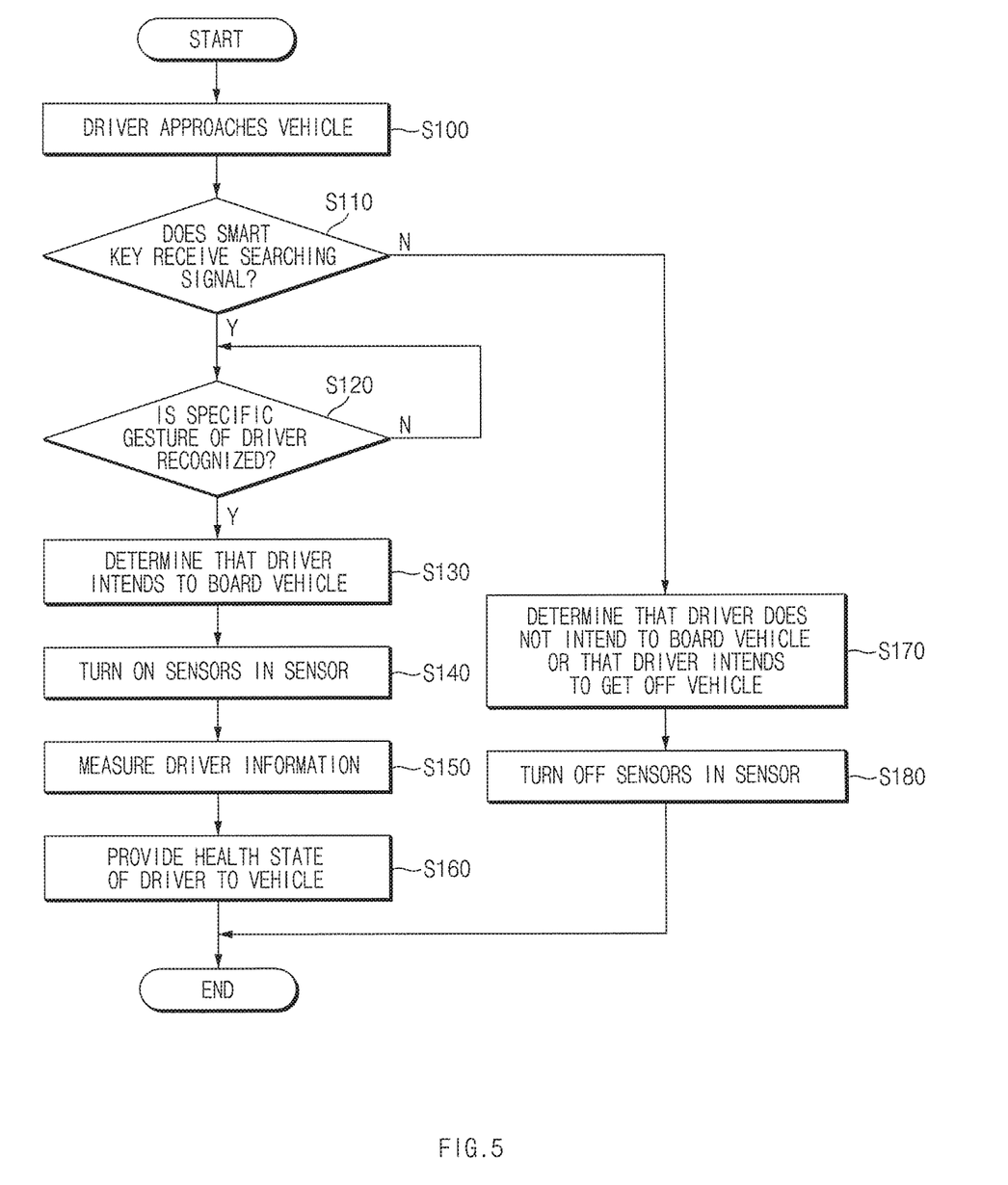
FIG. 5 is a flowchart illustrating a control method of a vehicle system, according to an embodiment of the present disclosure.

FIG. 5 is a flowchart illustrating a control method of a wearable device, according to an embodiment of the present disclosure.

Firstly, in operation S100, a driver approaches a vehicle in a state where the driver wears the wearable device 30. The smart key 20 may be embedded in the wearable device 30, and the wearable device 30 may be connected with the smart key 20 by a connector in hardware.

In addition, in operation S110, it is determined whether the smart key 20 in the wearable device 30 receives a searching signal (a LF signal) transmitted by the vehicle electronic device 10. In the case where the smart key 20 does not receive the searching signal transmitted by the vehicle electronic device 10 (N), if the driver does not board the vehicle, in operation S170, it may be determined that the driver just approaches the vehicle, without intending to board the vehicle or it may be determined that the driver intends to get off the vehicle if the driver boards the vehicle. Furthermore, in operation S180, the controller 36 may allow sensors in the sensor 37 not to operate.

In the case where the smart key 20 receives the searching signal transmitted by the vehicle electronic device 10 (Y), in operation S120, it is determined whether a specific gesture that the driver makes while approaching the vehicle is a specific gesture learned by the learning processor 35 of the wearable device 30. The specific gesture that the driver makes while approaching the vehicle may be sensed by the acceleration sensor 32 of the wearable device 30 and may be gesture information.

In the case where the specific gesture that the driver makes while approaching the vehicle is not the learned specific gesture (N), the driver may make a same gesture while approaching the vehicle again.

In the case where the specific gesture that the driver makes while approaching the vehicle is the learned specific gesture (Y), in operation S130, the controller 36 determines that the driver intends to board the vehicle.

In the case where it is determined that the driver intends to board the vehicle, in operation S140, the controller 36 may operate the sensors in the sensor 37. In the case where it is determined that the driver intends to board the vehicle, the operating sensors may include a PPG sensor. Since the sensors in the sensor 37 operate only if it is determined that the driver intends to board the vehicle, according to an embodiment of the present disclosure, a battery may be saved. In addition, in the case where it is determined that the driver does not intend to board the vehicle or in the case where it is determined that the driver intends to get off the vehicle, the controller 36 may allow the sensors not to operate, thereby saving the battery.

In the case where the sensors in the sensor 37 operate, in operation S150, information about a health state of the driver may be measured. The information about the health state of the driver may include one of a heart rate, a stress index, and vitality of the driver, and the measurement may take about one minute.

In operation S160, the measured information about the health state of the driver is provided to a control unit (ECU) of the vehicle. The information to be provided to the vehicle may be transmitted through a RF signal using BLE.

The present disclosure recognizes that a driver intends to board the vehicle, in the case where it is determined that a specific gesture that the driver makes while approaching a vehicle electronic device is the learned specific gesture, measures the health state of the driver by automatically operating the sensors a wearable device when it is recognized that the driver intends to board the vehicle, and provides the measured, information to the vehicle. Accordingly, the present disclosure provides the health state of the driver to the vehicle as well as saving the battery of the wearable device, and then the vehicle may contribute to the safety driving of the driver by recognizing the health state of the driver.

Figure 6:
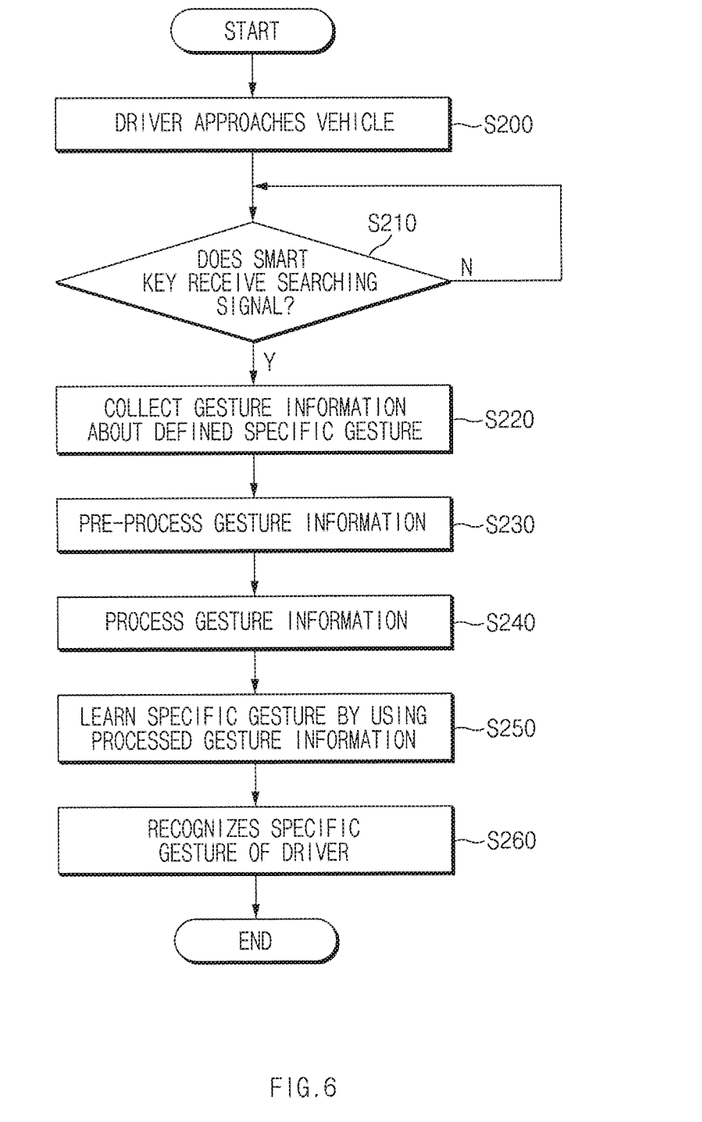
FIG. 6 is a flowchart illustrating a method of learning a specific gesture of a driver, according to an embodiment of the present disclosure.

FIG. 6 is a flowchart illustrating a method of learning a specific gesture of a driver, according to an embodiment of the present disclosure.

Firstly, in operation S200, a driver approaches a vehicle in a state where the driver wears the wearable device 30. The smart key 20 may be embedded in the wearable device 30, and the wearable device 30 may be connected with the smart key 20 by a connector in hardware.

In addition, in operation S210, it is determined whether the smart key 20 in the wearable device 30 receives a searching signal (a LF signal) transmitted by a vehicle. In the case where the searching signal (the LF signal) is not received, operation S210 is performed without learning.

In the case where the smart key 20 in the wearable device 30 receives the searching signal transmitted by the vehicle (Y), in operation S220, gesture information about a specific gesture that the driver makes while approaching the vehicle is collected.

The acceleration sensor 32 of the wearable device 30 may obtain gesture information about an X-axis, a Y-axis, and a Z axis by sensing the specific gesture that the driver makes while approaching the vehicle. Here, the specific gesture may include an operation of opening a door of the vehicle. The operation of opening the door of the vehicle may be roughly defined as an operation of three steps.

A. An operation of holding the handle of the vehicle door by extending the hand wearing a wearable device.
  B. An operation of pressing a handle button of the vehicle door.
  C. An operation of pulling the vehicle door toward a body of the driver to open the vehicle door.

In operation S230, the analysis processor 34 may apply a pre-processing algorithm to the gesture information, thereby reducing an effect on the noise of pieces of gesture information. A LPF, a Gaussian filter, or a moving average filter may be applied to reduce the effect on the noise.

In operation S240, the analysis processor 34 may apply a DTW algorithm to the pieces of gesture information, in which the effect on the noise is reduced, to process the data. Since an operation of opening a vehicle door is nearly similar for each driver, a pattern of data may be similar. However, a time period during which the operation is performed may be different. Similarity is measured by applying a DTW algorithm to pieces of data associated with operations performed during different time periods. The pieces of data having the similarity are processed through reconstruction.

In operation S250, the learning processor 35 may learn the specific gesture by using data, which is processed through the applying of the DTW algorithm. The leaning of the specific gesture may be learned by using a neural network algorithm. In addition, since the learning about a specific gesture is not made indefinitely, the specific gesture may be learned by using data (refer to FIG. 4) obtained until a learning error converges on a target value.

In operation S260, the controller 36 recognizes the learned specific gesture. If it is determined that the specific gesture that the driver makes when approaching the vehicle is the same as the learned specific gesture, it is recognized that the specific gesture that the driver makes when approaching the vehicle is the learned specific gesture.

Figure 7:
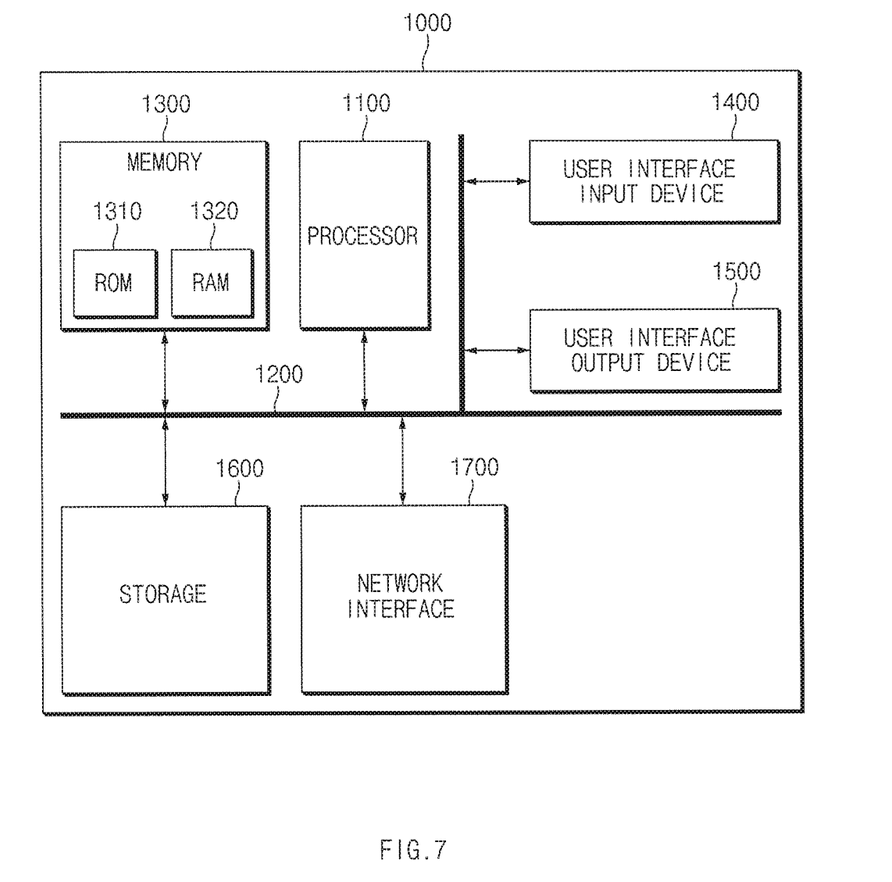
FIG. 7 is a block diagram illustrating a configuration of a computing system performing a method, according to an embodiment of the present disclosure.

FIG. 7 is a block diagram illustrating a configuration of a computing system performing a method, according to an embodiment of the present disclosure.

Referring to FIG. 7, a computing system 1000 may include at least one processor 1100, a memory 1300, a user interface input device 1400, a user interface output device 1500, a storage 1600, and a network interface 1700, which are connected with each other via a bus 1200.

The processor 1100 may be a central processing unit (CPU) or a semiconductor device that processes instructions stored in the memory 1300 and/or the storage 1600. Each of the memory 1300 and the storage 1600 may include various types of volatile or non-volatile storage media. For example, the memory 1300 may include a read only memory (ROM) and a random access memory (RAM).

Thus, the operations of the methods or algorithms described in connection with the embodiments disclosed in the specification may be directly implemented with a hardware module, a software module, or combinations thereof, executed by the processor 1100. The software module may reside on a storage medium (e.g., the memory 1300 and/or the storage 1600) such as a RAM, a flash memory, a ROM, an erasable and programmable ROM (EPROM), an electrically EPROM (EEPROM), a register, a hard disc, a removable disc, or a compact disc-ROM (CD-ROM). The storage medium may be coupled to the processor 1100. The processor 1100 may read out information from the storage medium and may write information in the storage medium. Alternatively, the storage medium may be integrated with the processor 1100. The processor and storage medium may reside in an application specific integrated circuit (ASIC). The ASIC may reside in a user terminal. Alternatively, the processor and storage medium may reside as a separate component in the user terminal.

The present disclosure may increase a recognition rate of driver's intention to get on and off a vehicle when a driver holding a smart key approaches the vehicle, and may allow a sensor of a wearable device to automatically turn on or off depending on the recognizing of the intention to get on and off a vehicle, thereby effectively using a battery. In addition, the present disclosure may operate a wearable device in conjunction with a vehicle such that a health state of a driver is determined before driving and during driving, thereby allowing the driver to perform safe driving.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, embodiments of the present disclosure are not intended to limit the technical spirit of the present disclosure, but provided only for the illustrative purpose. The scope of protection of the present disclosure should be construed by the attached claims, and all equivalents thereof should be construed as being included within the scope of the present disclosure.

What is claimed is:

1. A vehicle system transmitting information about a health state of a driver to a vehicle electronic device which communicates with a wearable device, the wearable device comprising:
   a smart key configured to receive a searching signal from the vehicle electronic device;
   an acceleration sensor configured to obtain gesture information about a specific gesture that the driver makes while approaching the vehicle electronic device;
   a learning processor configured to learn the specific gesture from the gesture information;
   a first controller configured to determine intention of the driver depending on whether the searching signal is received, and depending on whether the obtained gesture information is recognized as the specific gesture and to control on/off of a sensor measuring the information about the health state of the driver;
   a communication device configured to transmit the information about the health state of the driver to the vehicle electronic device; and
   an analysis processor configured to apply a dynamic time warping (DTW) algorithm to pieces of data associated with operations performed during different time periods.

2. The vehicle system of claim 1, wherein the smart key is embedded in the wearable device and is connected in hardware by a connector.

3. The vehicle system of claim 1, wherein the acceleration sensor obtains the gesture information about an X-axis, a Y-axis, and a Z-axis by sensing a specific gesture of gestures that the driver makes while approaching the vehicle electronic device.

4. The vehicle system of claim 1, wherein the specific gesture includes at least one of an operation of holding a handle of a vehicle door by extending a hand wearing the wearable device, an operation of pressing a handle button of the vehicle door, and an operation of pulling the vehicle door toward a body of the driver to open the vehicle door.

5. The vehicle system of claim 1, wherein the analysis processor is further configured to remove a noise by applying a pre-processing algorithm to the gesture information.

6. The wearable device of claim 1, wherein if the smart key receives the searching signal from the vehicle electronic device and if a gesture that the driver makes while approaching the vehicle electronic device is recognized as a specific gesture that the learning processor learns, the first controller determines that the driver intends to board a vehicle and turns on the sensor.

7. The wearable device of claim 1, wherein if the smart key does not receive the searching signal from the vehicle electronic device, the controller determines at least one of that the driver intends to get off a vehicle and that the driver does not intend to board the vehicle and turns off the sensor.

8. The wearable device of claim 1, wherein the information about the health state of the driver includes at least one of a heart rate, a stress index, and vitality of the driver.

9. The wearable device of claim 1, wherein the sensor includes a photo-plethysmo graphy (PPG) sensor.

10. The wearable device of claim 1, wherein the communication device transmits the information about the health state of the driver to the vehicle electronic device by using Bluetooth Low Energy (BLE).

11. The wearable device of claim 7, wherein when the sensor is turned off, the controller turns off the communication device.

12. The wearable device of claim 1, wherein when the communication device transmits the information about the health state of the driver to the vehicle electronic device, a second controller of the vehicle electronic device allows a display of the vehicle electronic device to output the information about the health state of the driver.

13. A control method of a vehicle system, which transmits information about a health state of a driver to a vehicle electronic device communicating with a wearable device, the method comprising:
   receiving, by a smart key embedded in the wearable device, a searching signal from the vehicle electronic device;
   determining, by a controller, whether a specific gesture that a driver makes while approaching the vehicle electronic device is a learned specific gesture;
   if the specific gesture that the driver makes while approaching the vehicle electronic device is the learned specific gesture, determining, by the controller, that the driver intends to board a vehicle;
   if it is determined that the driver intends to board the vehicle, operating, by the controller, a sensor measuring information about the health state of the driver; and
   transmitting, by a communication device, the information about the health state of the driver to the vehicle electronic device,
   wherein the determining whether a specific gesture that a driver makes is a learned specific gesture includes applying a dynamic time warping (DTW) algorithm to pieces of data associated with operations performed during different time periods.

14. The method of claim 13, wherein the receiving a searching signal from the vehicle electronic device includes:
   if the searching signal is not received, determining at least one of that the driver intends to get off a vehicle or that the driver does not intend to board the vehicle; and
   allowing the sensor not to operate.

15. The method of claim 13, wherein the determining whether a specific gesture that a driver makes is a learned specific gesture further includes:
   collecting gesture information about the specific gesture;
   removing a noise by applying a pre-processing algorithm to the gesture information;
   processing the gesture information;
   learning the specific gesture; and
   recognizing the learned specific gesture.

16. The method of claim 15, wherein the collecting gesture information includes:
   obtaining and collecting, by an acceleration sensor of the wearable device, the gesture information about an X-axis, a Y-axis, and a Z-axis.

17. The method of claim 15, wherein the specific gesture includes:
   collecting at least one of an operation of holding a handle of a vehicle door by extending a hand wearing the wearable device, an operation of pressing a handle button of the vehicle door, and an operation of pulling the vehicle door toward a body of the driver to open the vehicle door.

18. The method of claim 15, wherein the recognizing the learned specific gesture includes:
   recognizing that a specific gesture that the driver makes when approaching the vehicle electronic device is the learned specific gesture.

19. The method of claim 13, wherein the operating a sensor measuring information about the health state of the driver includes:
   measuring, by the sensor, information including at least one of a heart rate, a stress index, and vitality of the driver.

20. The method of claim 13, further comprising:
   after the transmitting the information about the health state of the driver to the vehicle electronic device, allowing, by a controller of the vehicle electronic device, a display of the vehicle electronic device to output the information about the health state of the driver.

* * * * *